United States Patent [19]

Asato et al.

[11] Patent Number: 4,886,828

[45] Date of Patent: Dec. 12, 1989

[54] $\Delta^{22}$-DERIVATIVES OF LL-F28249 COMPOUNDS

[75] Inventors: Goro Asato, Titusville; Susan Y. Tamura, Plainsboro, both of N.J.

[73] Assignee: American Cyanamid Company, Stamford, Conn.

[21] Appl. No.: 907,284

[22] Filed: Sep. 12, 1986

[51] Int. Cl.$^4$ .............................................. A61K 31/365
[52] U.S. Cl. ...................................... 514/450; 549/264
[58] Field of Search .......................... 549/264; 514/450

[56] References Cited

U.S. PATENT DOCUMENTS

| Re. 32,034 | 11/1985 | Chabala et al. | 549/264 |
| 4,328,335 | 5/1982 | Mrozik | 536/7.1 |
| 4,378,353 | 3/1983 | Goegelman et al. | 435/119 |

FOREIGN PATENT DOCUMENTS

| 74758 | 3/1983 | European Pat. Off. | 549/264 |
| 170006 | 2/1986 | European Pat. Off. | |
| 2166436 | 5/1986 | United Kingdom | |

Primary Examiner—Glennon H. Hollrah
Assistant Examiner—Amelia A. Owens
Attorney, Agent, or Firm—Estelle J. Tsevdos

[57] ABSTRACT

The present invention relates to novel derivatives of LL-F28249 compounds. These LL-F28249 compounds preferably are derived via a controlled microbiological fermentation of *Streptomyces cyaneogriseus* subsp. *non-cyanogenus* having deposit accession numer NRRL 15773. The derivatives of the present invention have the 23-hydroxy group react to form a double bond in the 22,23 position. The novel derivatives of the present invention possess activity as anthelmintic, ectoparasitic, insecticidal, acaricidal and nematicidal agents. They also are useful in areas of human and animal health and in agricultural crops.

14 Claims, No Drawings

$\Delta^{22}$-DERIVATIVES OF LL-F28249 COMPOUNDS

BACKGROUND OF THE INVENTION

The present invention relates to new derivatives of the antibiotics collectively defined as LL-F28249. These antibiotics preferably are produced by the fermentation of the microorganism *Streptomyces cyaneogriseus* subsp. *noncyanogenus*, deposited in NRRL under deposit accession no. 15773. The LL-F28249 compounds and the method for their production are disclosed in European Patent Application Publication No. 170,006, incorporated herein by reference.

The present invention further relates to methods and compositions for preventing, treating or controlling helminth, ectoparasite, insect, acarid and nematode infections in warm-blooded animals and agricultural crops by administering thereto prophylactically, therapeutically or pharmaceutically effective amount of the present $\Delta^{22}$-LL-F28249 agents (compounds), mixtures thereof or the pharmaceutically and pharmacologically-acceptable salts thereof.

These infections not only cause devastating effects to animals but also seriously effect the economics of farmers in raising meat-producing animals such as swine, sheep, cattle, goats, rabbits and poultry. Further, such infections are a source of great concern for companion animals such as horses, dogs and cats. Therefore, effective methods for the treatment and prevention of these diseases constantly are being sought.

SUMMARY OF THE INVENTION

The present invention provides novel $\Delta^{22}$-derivatives of the compounds designated LL-F28249 and represented by the following structural formula,

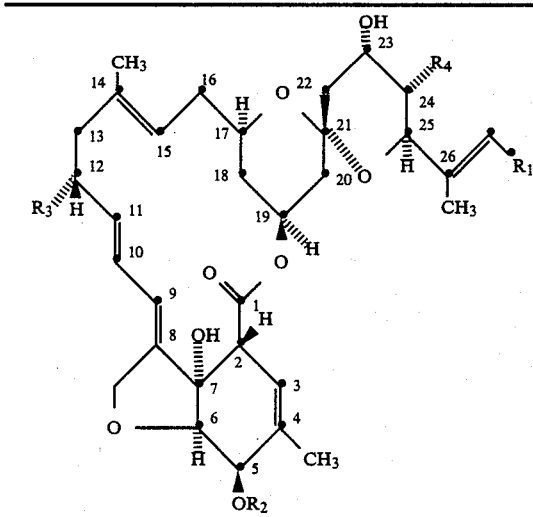

| Component | $R_1$ | $R_2$ | $R_3$ | $R_4$ |
|---|---|---|---|---|
| LL-F28249α | CH(CH$_3$)$_2$ | H | CH$_3$ | CH$_3$ |
| LL-F28249β | CH$_3$ | H | CH$_3$ | CH$_3$ |
| LL-F28249γ | CH$_3$ | CH$_3$ | CH$_3$ | CH$_3$ |
| LL-F28249ε | CH(CH$_3$)$_2$ | H | H | CH$_3$ |
| LL-F28249δ | CH$_2$CH$_3$ | H | CH$_3$ | CH$_3$ |
| LL-F28249θ | CH(CH$_3$)$_2$ | H | CH$_3$ | CH$_2$CH$_3$ |
| LL-F28249ζ | CH(CH$_3$)$_2$ | H | CH$_2$CH$_3$ | CH$_3$ |
| LL-F28249λ | CH(CH$_3$)$_2$ | CH$_3$ | CH$_3$ | CH$_3$ |

The compounds of the present invention are represented by structural formula (I),

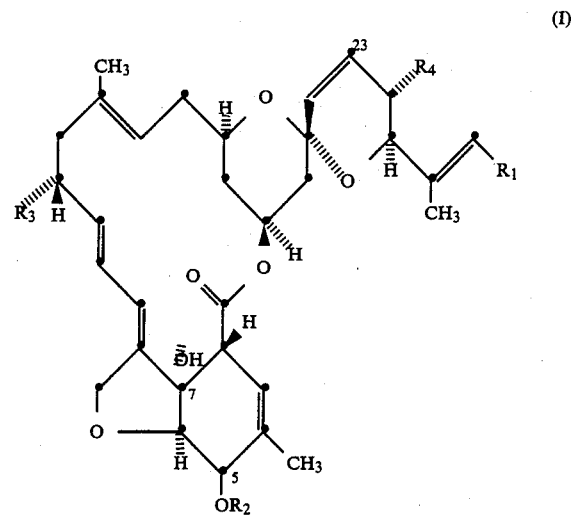

wherein $R_1$ is methyl, ethyl or isopropyl; $R_2$ is hydrogen or methyl; $R_3$ is hydrogen, methyl or ethyl; $R_4$ is methyl or ethyl; and the pharmaceutically and pharmacologically acceptable salts thereof.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for effective such therapy. For instance, U.S. Application for Letter patent Ser. Nos. 907186, 907283, 907188, 907281, 907259 and 907187 of Asato and Asato et al, filed concurrently herewith and incorporated herein by reference thereof, provide novel compounds for such uses.

U.S. Pat. No. 3,950,360, Aoki et al, Apr. 13, 1976, discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. British Patent Application 2166436A of Ward et al relates to antibiotics also.

The present compounds or the pharmaceutically and pharmacologically-acceptable salts thereof exhibit excellent and effective treatment and/or prevention of these serious diseases of warm-blooded animals.

It is an object of the present invention, therefore, to provide novel $\Delta^{22}$-compounds of the LL-F28249 series of compounds.

It is a further object of the present invention to provide novel methods for the treatment, prevention or control of helmintic, ectoparasitic, insect, acarid and nematode infections and infestations in warm-blooded animals and agricultural crops.

It also is an object of the present invention to provide novel compositions to effectively control, prevent or treat said diseases in warm-blooded animals.

These and further objects will become apparent by the below-provided detailed description of the invention.

DETAILED DESCRIPTION OF THE INVENTION

The compounds of the invention are represented by structural formula (I),

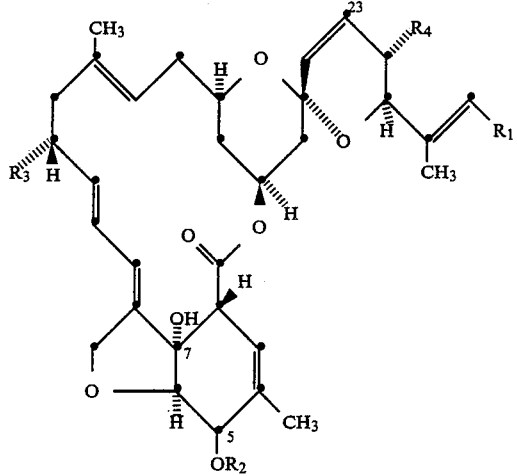

wherein $R_1$ is methyl, ethyl or isopropyl; $R_2$ is hydrogen or methyl; $R_3$ is hydrogen, methyl or ethyl; $R_4$ is methyl or ethyl; and the pharmaceutically and pharmacologically acceptable salts thereof.

Preferably, $R_1$ is isopropyl; $R_2$ is hydrogen or methyl; $R_3$ is methyl; and $R_4$ is methyl. Most preferred compound includes $R_1$ as isopropyl, $R_2$ as hydrogen, $R_3$ as methyl and $R_4$ as methyl.

The $\Delta^{22}$-derivatives of LL-F28249 are prepared by eliminating the 23-hydroxyl group and introducing a double bond at the 22,23 position.

Removal of the 23-hydroxyl group of LL-F28249α, as example of the compounds, is accomplished by initially protecting the 5-hydroxyl group. This protected compound then is derivatized by having the 23-hydroxyl group react with a substituted thiocarbonyl halide, after which the 5-hydroxyl protecting group is removed and 23-oxy group is eliminated to afford the $\Delta^{22}$-LL-F28249α compound.

Suitable protecting groups are trisubstituted silyl groups such as t-butyldimethylsilyl and trimethylsilyl, or trisubstituted silyloxyacetyl groups, such as t-butyldimethylsilyloxy acetyl groups. The protecting groups, however, are not limited to these groups since other useful protecting groups such as acyl and substituted acyl, such as acetyl, trifluoroacetyl, chloroacetyl, trichloroacetyl, phenoxyacetyl and the like, are also useful in the present process.

One of the preferred protecting groups is t-butyldimethylsilyl. This group is attached to the 5-hydroxyl group by reacting an unprotected 5-hydroxy F-28249 compound with t-butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/$C_8$ rapid analysis column.

Another preferred protecting group is t-butyldimethylsilyloxy acetyl group. This group is attached to the 5-hydroxyl group by combining the unprotected F-28249 compound in an aprotic solvent such as methylene chloride, toluene, ethyl acetate, tetrahydrofuran, ethylenedichloride and the like, containing a tertiary amine, such as pyridine or triethylamine, and adding the protecting agent in the form of an acid halide. The reaction is conducted at a temperature of about 0° C. to 30° C. and is monitored by HPLC for completion.

When the t-butyldimethylsilyloxy acetyl type of protecting group, in the form of an acid halide, is combined with the LL-F28249 compound in an aprotic solvent in the presence of an acid acceptor, as indicated hereinabove, trisubstituted silyl chloride is used. Acid anhydrides also are useful in the present invention instead of the acid chlorides in pyridine containing a catalytic amount of 4-N,N-dimethylaminopyridine.

The silyl protecting group is removed by stirring a protected 5-hydroxy F28249 compound in a lower alkanol such as methanol at 0° C. to room temperature for about 0.5 hour to an hour in the presence of an acid such as p-toluenesulfonic acid. If the protecting group is a silyloxyacetyl group, the silyl group is removed with acid as described above, and the hydroxyacetyl group is cleaved with an equivalent of base such as sodium methoxide in methanol at 0° C. to toom temperature in 0.5 hour to several hours. The silyloxyacetyl group may also be removed in one step by treatment with sodium methoxide at room temperature until the reaction is complete. Similarly, other acyl protecting groups are removed by base treatment.

With the 5-hydroxyl protected, the 23-hydroxyl group is reacted with a substituted thiocarbonyl halide of the formula:

wherein X is a halogen such as chlorine, bromine or iodine, with chloride being preferred; and R is a substituted phenoxy, wherein said substitution is a lower alkyl, preferably 4-methyl.

This reaction results in the preparation of a compound with a 23-thiocarbonyloxy group. The reaction is carried out at temperatures of about 0° C. to 50° C. for about 0.5–2.0 hours in an aprotic solvent such as methylene chloride, toluene, ethylacetate, tetrahydroguran, ethylenedichloride and the like and a tertiary amine such as pyridine or triethylamine is pyridine and the preferred proton acceptor is 4-dimethylaminopyridine (also functioning as a catalyst). Generally, the thiocarbonyl halide is used in about 10% to 500% molar excess.

The elimination reaction of the thiocarbonyloxy group is carried out in an inert high-boiling solvent such as 1,2-dichlorobenzene or trichlorobenzene at about 150° C.–225° C. for about 0.5 to 4.0 hours. The solvent is removed in vacuo, and the product is purified by techniques, such as chromatography known to those skilled in the art. The following schematically illustrates the process.

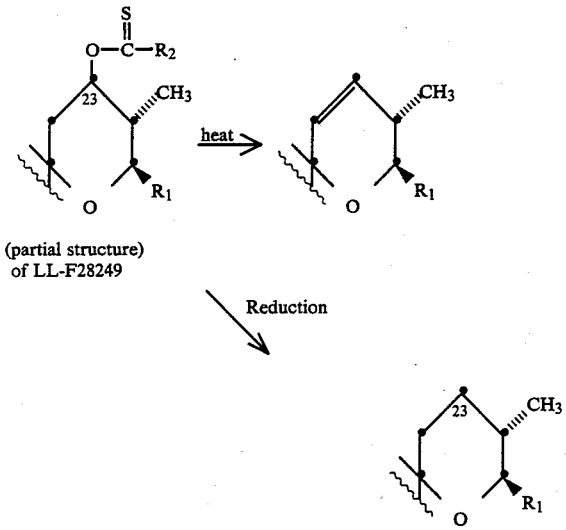

(partial structure) of LL-F28249

The thiocarbonyloxy group may also be reduced with reducing agents such as tributyltin hydride in the presence of a free radical initiator such as azobisisobutyronitrile to afford a 23-deoxy-LL-F28249 compound.

Obviously, if the $\Delta^{22}$-LL-F28249 compound wherein $R_1$ and $R_2$ are methyl is desired, the starting material is LL-F28249$\gamma$ and requires no protecting group. Thus, LL-F28249$\gamma$ is reacted directly with a substituted thiocarbonyl halide, and the resulting product is further processed in the manner described hereinabove to afford $\Delta^{22}$-LL-F28249$\gamma$.

The compounds of the present invention are useful as anthelmintics, ectoparasiticides, insecticides, acaricides and nematicides.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum primarily attack the intestinal tract, while others, such as Haemonchus and Ostertagia, are most prevalent in the stomach. Still others, such as Dictyocaulus, are found in the lungs. However, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and, if left untreated, may result in death of the infected host. The LL-F28249 compound derivatives of the present invention unexpectedly have high activity against these parasites. Additionally, the compounds of this invention also are active against Dirofilaria in dogs, Nematospiroides, Syphacia, Aspiculuris in rodents, arthropod ectoparasites such as ticks, mites, lice, fleas, blowfly, of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites (collectively includes ecto and/or endoparasites) which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle Attagenus sp. and the housefly *Musca domestica*.

Insect pests of stored grains such as Tribolium sp., Tenebrio sp., and of agricultural plants such as spider mites (Tetranychus sp.), aphids (Acyrthiosiphon sp.), southern army worms, tobacco budworms, boll weevils migratory orthopterans, such as locusts and immature stages of insects living on plant tissue are controlled by the present compounds, as well as the control of soil nematodes and plant parasites such as Meloidogyne sp.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the $\Delta^{22}$-LL-F28249 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the invention may be administered to animals parenterally such as by intraruminal, intramuscular, intratracheal or subcutaneous injection. In such an event, the active compound is dissolved or dispersed in a liquid carrier vehicle.

For parenteral administration, the active compound is suitably admixed with an acceptable vehicle, preferably a vegetable oil such as peanut oil, cotton seed oil or the like. Other parenteral vehicles such as organic preparations using solketal, glycerol formal and aqueous parenteral formulation also are used. The active LL-F28249 compound derivative or derivatives are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention, treatment or control of diseases caused by other parasites (collectively both ecto and/or endoparasites). For example, arthropod parasites such as ticks, lice, fleas, mites and other biting insects in domesticated animals and poultry are controlled by the present compounds. These compounds also are effective in treatment of parasitic diseases which occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg per kg of animal body weight, such total dose being given at one time or in divided doses over a relatively short period of time (1-5 days). The preferred compounds of the invention give excellent control of such parasites in animals by administering about 0.025 mg to 3 mg per kg of animal body weight in a single dose. Repeat treatments are given as required to combat reinfections and are dependent upon the species of parasite and the husbandry techniques being employed. The techniques for administering these materials to animals are known to those skilled in the veterinary field.

When the compounds described herein are administered as a component of animals' feed or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment and control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds of this invention also are useful in combating agricultural pests that inflict damage upon growing or stored crops. The present compounds are applied, using known techniques such as sprays, dusts, emulsions and the like, to the growing or stored crops to effect protection from agricultural pests.

The present invention is illustrated by the following examples which are illustrative of said invention and not limitative thereof.

EXAMPLE 1

5-O-t-Butyldimethylsilyl-LL-F28249α

In 500 mL of $CH_2Cl_2$, 70 g of LL-F28249α is stirred with 82.04 g of imidazole at 20° C. under $N_2$ atmosphere. Then, 43 g of t-butyldimethylsilyl chloride in 400 mL of $CH_2Cl_2$ is added over 5 minutes. After an hour, the reaction is assayed for completion by high performance liquid chromatography (HPLC), using 50% $CH_3CN$/50% $H_2O$ in a curved gradient mode over 10 minutes on a Whatman $C_8$-RAC column at 1 mL/min. Another 3 g of t-butyldimethylsilyl chloride is added, and after 3 hours, the composition is 92.3% product, 0.3% LL-F28249α and 1.16% disilylated material. The mixture is diluted with $CH_2Cl_2$ and poured into 2 L of $H_2O$. The $CH_2Cl_2$ layer then is separated. The aqueous portion is extracted with 2 L of $CH_2Cl_2$, and the combined organic layers are dried ($Na_2SO_4$). The $CH_2Cl_2$ is evaporated in vacuo to afford 116 g of the title compound that is identified by mass spectrometry and nuclear magnetic resonance (NMR) spectrometry.

EXAMPLE 2

23-O-[(4-Methylphenoxy)thiocarbonyl]-LL-F28249α

In 4 mL of dry pyridine, 291.7 mg of 5-O-t-butyldimethylsilyl-LL-F28249α and 9.7 mg of 4-dimethylaminopyridine are stirred under $N_2$ atmosphere at 0° C. while 0.62 mL of O-(4-methylphenyl)chlorothioformate is added dropwise. After the addition is completed, the mixture is stirred at room temperature (about 25° C.) until a solution is obtained. The solution is then heated at 45° C. in an oil bath for 1 hour, cooled and quenched with 1 mL of $H_2O$ at ice bath temperature. The mixture is stirred for 10 minutes at room temperature, diluted with 30 mL of $H_2O$ and extracted with 5×15 mL of $Et_2O$. The combined $Et_2O$ extracts are washed successively with $H_2O$ (2×10 mL), $CuSO_4$ solution, $H_2O$ (2×10 mL), 10% $Na_2CO_3$ solution and brine. The ether solution is dried (MgSO4), filtered and evaporated to dryness. The residue is mixed with toluene, evaporated to dryness to remove traces of pyridine and chromatographed over silica gel using 6% EtOAc in hexane. The crude product is dissolved in 3 mL of MeOH containing 30.4 mg of p-toluenesulfonic acid, and the mixture is stirred in an ice bath under $N_2$ atmosphere for 2 hours. The mixture is then neutralized with NaHCO3 solution, diluted with $H_2O$ and extracted with ether several times. The combined ether extracts are washed with brine and dried (MgSO4). After evaporating to dryness, the residue is chromatographed on silica gel using 5% EtOAc in $CH_2Cl_2$ containing 5 drops of i-PrOH/100 mL of solvent mixture. Removal of solvents from the desired fractions affords 79.8 mg of the title compound that is characterized by mass spectrometry and NMR spectroscopy.

EXAMPLE 3

$\Delta^{22}$-LL-F28249$\alpha$

In 1.5 mL of o-dichlorobenzene, 73.4 mg of 23-O[(4-methylphenoxy)thiocarbonyl]-LL-F28249$\alpha$ is heated at reflux temperature under $N_2$ atmosphere for 3 hours. The solution is cooled. The solvent then is removed in vacuo, and the residue is chromatographed on silica gel using 7% EtOAc in $CH_2Cl_2$ containing 10 drops of i-PrOH per 100 mL of solvent mixture. Evaporation of the solvents from the desired fraction affords 28.4 mg of the title compound that is characterized by mass spectrometry and NMR spectroscopy.

EXAMPLES 4 AND 5

23-O[(4-Methylphenoxy)thiocarbonyl]-LL-F28249$\gamma$

Following the procedure of Example 2, LL-F28249$\gamma$ is reacted with O-(4-methylphenyl)chlorothioformate to afford the title compound that is identified by mass spectrometry and NMR spectroscopy.

Similarly, O[(4-methylphenoxy)thiocarbonyl]-LL-F28249$\lambda$ is prepared.

EXAMPLES 6 AND 7

$\Delta^{22}$-LL-F28249$\gamma$

By the procedure of Example 3, the title compound is prepared from 23-O[(4-methylphenoxy)thiocarbonyl]-LL-F28249$\gamma$. The title compound is identified by mass spectrometry and NMR spectroscopy.

Similarly, $\Delta^{22}$-LL-F28249$\lambda$ is prepared by this procedure.

EXAMPLES 8-12

Using the method of Example 1 to protect the 5-hydroxy group, followed by derivatization of the 23-hydroxy group by the method of Example 2 and decomposing the 23-O[(4-methylphenoxy)thiocarbonyl]-LL-F28249 compounds by the method of Example 3, the following commpounds are prepared:

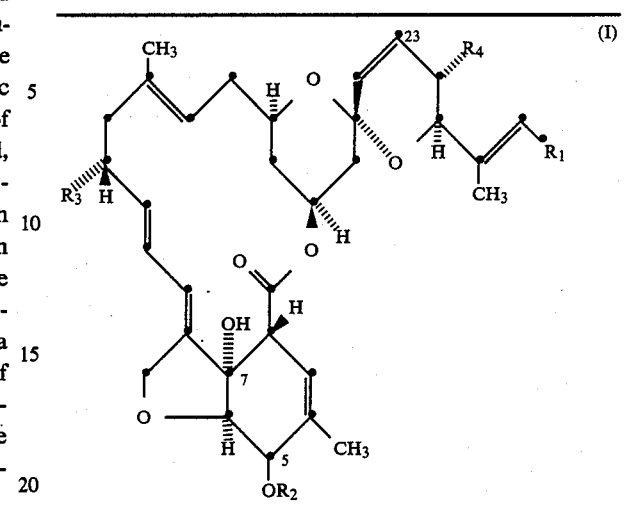

| $R_1$ | $R_2$ | $R_3$ | $R_4$ |
|---|---|---|---|
| $CH_3$ | H | $CH_3$ | $CH_3$ |
| $CH_3(CH_3)_2$ | H | H | $CH_3$ |
| $CH_2CH_3$ | H | $CH_3$ | $CH_3$ |
| $CH(CH_3)_2$ | H | $CH_3$ | $CH_2CH_3$ |
| $CH(CH_3)_2$ | H | $CH_2CH_3$ | $CH_3$ |

What is claimed is:

1. A compound represented by structural formula (I),

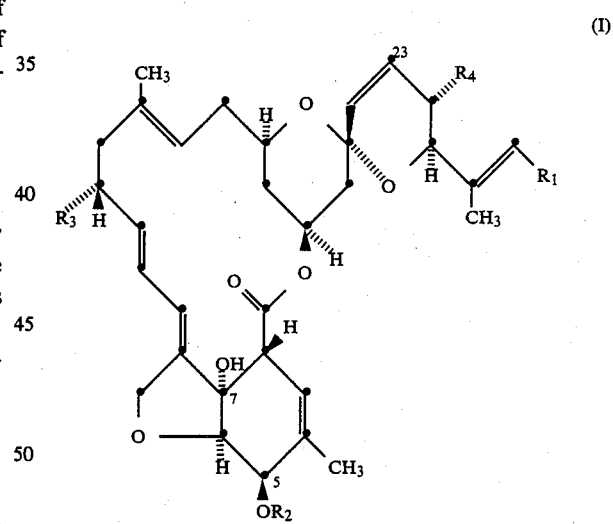

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof.

2. A compound according to claim 1, wherein $R_1$ is isopropyl; $R_2$ is hydrogen or methyl; $R_3$ is methyl; and $R_4$ is methyl.

3. A compound according to claim 2, wherein $R_1$ is isopropyl; $R_2$ is hydrogen; $R_3$ is methyl; and $R_4$ is methyl.

4. A method for the prevention, treatment or control of parasitic infections in warm-blooded animals, said method comprising: orally, topically or parenterally administering to an animal infected with parasites, a parasiticidally-effective amount of a compound represented by structural formula (I)

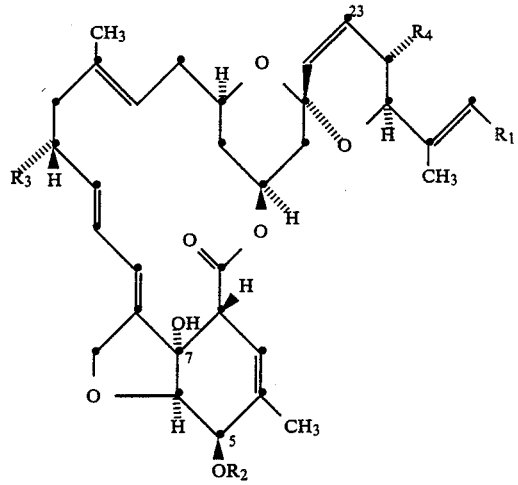
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof.

5. A method according to claim 4, wherein said compound has $R_1$ as isopropyl; $R_2$ is hydrogen or methyl; $R_3$ is methyl; and $R_4$ is methyl.

6. A method according to claim 5, wherein said compound has $R_1$ as isopropyl; $R_2$ is hydrogen; $R_3$ is methyl; and $R_4$ is methyl.

7. A method for protecting crops, trees, shrubs, stored grain and ornamentals from attack by insects and acarids which infect them, said method comprising: applying an acaricidally or insecticidally-effective amount of a compound represented by structural formula (I),

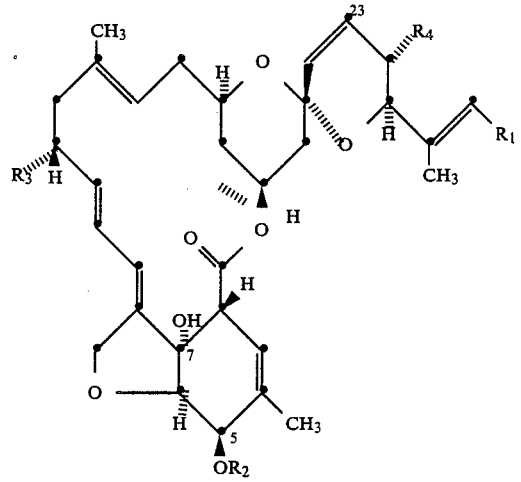
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof.

8. A method according to claim 7, wherein said compound is applied to the foliage of crops and plants, the soil in which they are grown or the trunk thereof.

9. A method according to claim 8, wherein said compound has $R_1$ as isopropyl; $R_2$ is hydrogen or methyl; $R_3$ is methyl; and $R_4$ is methyl.

10. A method according to claim 9, wherein said compound has $R_1$ as isopropyl; $R_2$ is hydrogen; $R_3$ is methyl; and $R_4$ is methyl.

11. A method for the control of plant nematodes, said method comprising: applying to the foliage of plants, the soil in which they are grown or into the trunks thereof, a nematocidally-effective amount of a compound represented by structural formula (I),

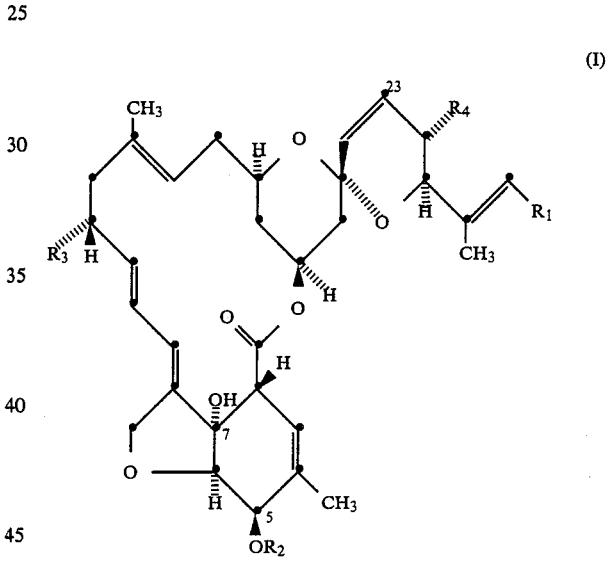
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof.

12. A method according to claim 11, wherein said compound has $R_1$ as isopropyl; $R_2$ is hydrogen or methyl; $R_3$ is methyl; and $R_4$ is methyl.

13. A method according to claim 12, wherein said compound has $R_1$ as isopropyl; $R_2$ is hydrogen; $R_3$ is methyl; and $R_4$ is methyl.

14. A composition comprising: a pharmacologically, acaricidally or insecticidally effective amount of a compound represented by structural formula (I),

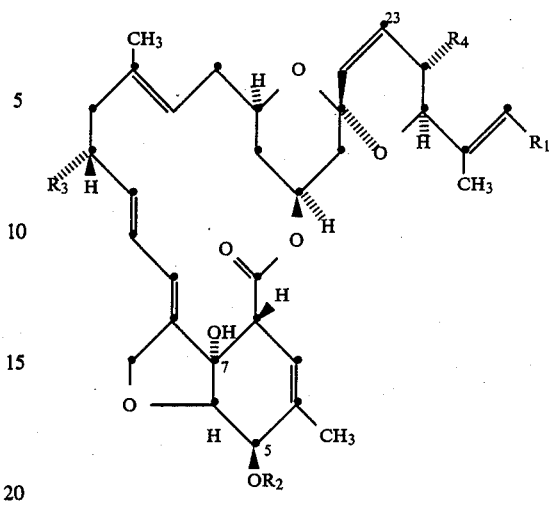

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof: and an inert carrier; wherein said composition is used to control endo- or ectoparasitic pests which infect warm-blooded animals or to control acarid or insect pests which infest agricultural crops.

* * * * *